United States Patent
Spencer et al.

(10) Patent No.: US 10,322,229 B2
(45) Date of Patent: *Jun. 18, 2019

(54) MULTI-LANGUAGE / MULTI-PROCESSOR INFUSION PUMP ASSEMBLY

(71) Applicant: DEKA Products Limited Partnership, Manchester, NH (US)

(72) Inventors: Geoffrey P. Spencer, Manchester, NH (US); Robert J. Bryant, Manchester, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/383,595

(22) Filed: Dec. 19, 2016

(65) Prior Publication Data

US 2017/0095609 A1    Apr. 6, 2017

Related U.S. Application Data

(63) Continuation of application No. 14/263,318, filed on Apr. 28, 2014, now Pat. No. 9,522,226, which is a
(Continued)

(51) Int. Cl.
*A61M 5/142* (2006.01)
*A61M 5/145* (2006.01)
(Continued)

(52) U.S. Cl.
CPC ...... *A61M 5/1452* (2013.01); *A61M 5/16854* (2013.01); *G06F 17/5054* (2013.01); *G06F 19/00* (2013.01); *G06F 19/3468* (2013.01); *A61M 2005/14208* (2013.01); *A61M 2005/14292* (2013.01);
(Continued)

(58) Field of Classification Search
CPC .......... A61M 5/14244; A61M 2205/18; A61M 5/16854; A61M 2005/14268; A61M 2205/50; A61M 5/1452; A61M 2205/3569; A61M 2205/8206; A61M 5/14248; A61M 2005/14292; A61M 2205/16; A61M 2005/14208; A61M 2205/17; A61M 2205/52; A61M 5/1723; A61M 5/1413;
(Continued)

(56) References Cited

U.S. PATENT DOCUMENTS 115,917 A    6/1871 Wharton
4,529,401 A    7/1985 Leslie et al.
(Continued)

*Primary Examiner* — Bhisma Mehta
*Assistant Examiner* — Matthew A Engel
(74) *Attorney, Agent, or Firm* — McCormick, Paulding & Huber LLP

(57) ABSTRACT

An infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. The processing logic includes a primary microprocessor configured to execute one or more primary applications written in a first computer language; and a safety microprocessor configured to execute one or more safety applications written in a second computer language.

21 Claims, 3 Drawing Sheets

Related U.S. Application Data continuation of application No. 13/621,365, filed on Sep. 17, 2012, now Pat. No. 8,708,960, which is a continuation of application No. 12/249,600, filed on Oct. 10, 2008, now Pat. No. 8,267,892.

(51) Int. Cl.

| | | |
|---|---|---|
| *A61M 5/168* | (2006.01) | |
| *G06F 17/50* | (2006.01) | |
| *G06F 19/00* | (2018.01) | |

(52) U.S. Cl.
CPC ..... *A61M 2205/16* (2013.01); *A61M 2205/17* (2013.01); *A61M 2205/18* (2013.01); *A61M 2205/332* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/702* (2013.01); *A61M 2205/8206* (2013.01); *G06F 2217/68* (2013.01)

(58) Field of Classification Search
CPC .... A61M 2205/3592; A61M 2230/201; A61M 5/1456
USPC .............................. 604/65–67, 131–155, 257
See application file for complete search history.

(56) References Cited

U.S. PATENT DOCUMENTS

| | | | |
|---|---|---|---|
| 4,685,902 A | 8/1987 | Edwards et al. | |
| 5,207,642 A | 5/1993 | Orkin et al. | |
| 5,522,803 A | 6/1996 | Teissen-Simony | |
| 5,533,981 A | 7/1996 | Mandro et al. | |
| 5,712,795 A | 1/1998 | Layman et al. | |
| 5,882,047 A | 3/1999 | Ostrander et al. | |
| 6,283,949 B1 | 9/2001 | Roorda | |
| 6,685,674 B2 | 2/2004 | Douglas et al. | |
| 6,904,324 B2 | 6/2005 | Bishay | |
| 7,527,052 B2* | 5/2009 | Hickle | A61M 16/01 128/202.22 |
| 8,518,021 B2* | 8/2013 | Stewart | A61M 5/14228 604/500 |
| 8,721,584 B2* | 5/2014 | Braithwaite | A61M 5/1723 604/66 |
| 9,552,053 B2* | 1/2017 | O'Connor et al. | G06F 1/26 |
| 2002/0019606 A1* | 2/2002 | Lebel | A61M 5/172 604/66 |
| 2002/0095138 A1 | 7/2002 | Lynch et al. | |
| 2002/0120231 A1 | 8/2002 | Douglas et al. | |
| 2002/0161332 A1 | 10/2002 | Ramey | |
| 2002/0169419 A1 | 11/2002 | Steg | |
| 2003/0097232 A1* | 5/2003 | McClendon | A61M 5/142 702/114 |
| 2003/0205587 A1 | 11/2003 | Tribe et al. | |
| 2004/0077997 A1* | 4/2004 | Jasperson | A61M 5/14276 604/67 |
| 2005/0065464 A1* | 3/2005 | Talbot | A61B 5/01 604/66 |
| 2005/0085760 A1* | 4/2005 | Ware | A61M 1/3441 604/4.01 |
| 2005/0234382 A1 | 10/2005 | Tonelli et al. | |
| 2005/0242126 A1 | 11/2005 | Izoe | |
| 2006/0208695 A1 | 9/2006 | Weinstein et al. | |
| 2007/0106218 A1 | 5/2007 | Yodfat et al. | |
| 2007/0129621 A1 | 6/2007 | Kellogg et al. | |
| 2007/0219496 A1* | 9/2007 | Kamen | G05D 7/0647 604/131 |
| 2007/0244469 A1 | 10/2007 | Ozeri et al. | |
| 2008/0077081 A1 | 3/2008 | Mounce et al. | |
| 2008/0183060 A1* | 7/2008 | Steil | A61B 5/14532 600/365 |
| 2008/0215029 A1 | 9/2008 | Rake et al. | |
| 2008/0255517 A1 | 10/2008 | Nair et al. | |
| 2009/0069785 A1 | 3/2009 | Miller et al. | |
| 2009/0082835 A1 | 3/2009 | Jaax et al. | |
| 2009/0118683 A1 | 5/2009 | Hanson et al. | |
| 2009/0156990 A1 | 6/2009 | Wenger et al. | |
| 2009/0259217 A1* | 10/2009 | Hyde | A61M 5/14276 604/891.1 |
| 2009/0275887 A1 | 11/2009 | Estes | |
| 2010/0010443 A1 | 1/2010 | Morgan et al. | |
| 2010/0030293 A1* | 2/2010 | Sarkar | A61B 5/046 607/18 |
| 2010/0078016 A1 | 4/2010 | Andrieux et al. | |
| 2010/0078026 A1 | 4/2010 | Andrieux et al. | |
| 2010/0137790 A1 | 6/2010 | Yodfat | |
| 2010/0286467 A1 | 11/2010 | Pesach et al. | |

\* cited by examiner

MULTI-LANGUAGE / MULTI-PROCESSOR INFUSION PUMP ASSEMBLY

CROSS REFERENCE TO RELATED APPLICATIONS

This application is a continuation of U.S. patent application Ser. No. 14/263,318, filed on Apr. 28, 2014, which is a continuation of Ser. No. 13/621,365 filed on Sep. 17, 2012, now U.S. Pat. No. 8,708,960, which is a continuation of U.S. patent application Ser. No. 12/249,600, filed on Oct. 10, 2008, now U.S. Pat. No. 8,267,892, each of which is hereby incorporated herein by reference in its entirety.

TECHNICAL FIELD

This disclosure relates to infusion pump assemblies and, more particularly, to infusion pump assemblies that include multiple microprocessors.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

Unfortunately, the failure of a microprocessor included within a single-processor infusion pump assembly may result in the infusion pump assembly ceasing to operate. Additionally, in an infusion pump assembly that includes multiple microprocessors executing code written in a common language, an undisclosed problem within the common-language code may compromise the operation of all microprocessors included within the multi-processor infusion pump assembly.

SUMMARY OF DISCLOSURE

In a first implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to provide one or more control signals to the motor assembly. The one or more control signals are processable by the motor assembly to effectuate the dispensing of the at least a portion of the infusible fluid contained within the reservoir assembly. The processing logic includes a primary microprocessor configured to execute one or more primary applications written in a first computer language; and a safety microprocessor configured to execute one or more safety applications written in a second computer language.

One or more of the following features may be included. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic. The primary power supply may be a first battery; and the backup power supply may be a super capacitor assembly.

The processing logic may include one or more circuit partitioning components configured to divide the processing logic into primary processing logic and backup processing logic. The primary processing logic may include the primary microprocessor. The backup processing logic may include the safety microprocessor.

The one or more circuit partitioning components may include one or more of a diode assembly and a current limiting assembly. The diode assembly may be configured to allow the primary power supply to charge the backup power supply while prohibiting the backup power supply from providing backup electrical energy to the primary processing logic in the event that the primary power supply fails to provide the primary electrical energy to the primary processing logic.

The one or more primary applications written in the first computer language may be chosen from the group consisting of an operating system, an executive loop and a software application. The one or more safety applications written in the second computer language may be chosen from the group consisting of an operating system, an executive loop and a software application.

The primary power supply may be configured to provide electrical energy to one or more subsystems included within the infusion pump assembly. The primary power supply and the backup power supply may be configured to provide electrical energy to an audio system included within the infusion pump assembly. The audio system may be configured to provide an escalating alarm sequence in the event of a loss of a beacon signal, wherein the escalating alarm sequence includes at least a low-intensity alarm and a high-intensity alarm.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to provide one or more control signals to the motor assembly. The one or more control signals are processable by the motor assembly to effectuate the dispensing of the at least a portion of the infusible fluid contained within the reservoir assembly. The processing logic includes one or more circuit partitioning components configured to divide the processing logic into primary processing logic and backup processing logic. A primary microprocessor is included within the primary processing logic and configured to execute one or more primary applications written in a first computer language. A safety microprocessor is included within the backup processing logic and configured to execute one or more safety applications written in a second computer language.

One or more of the following features may be included. The one or more primary applications written in the first computer language may be chosen from the group consisting of an operating system, an executive loop and a software application. The one or more safety applications written in the second computer language may be chosen from the group consisting of an operating system, an executive loop and a software application. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

In another implementation, a computer program product resides on a computer readable medium having a plurality of instructions stored on it. When executed by a processor, the instructions cause the processor to perform operations including receiving, on a first microprocessor executing one or more applications written in a first computer language, an initial command processable by the one or more applications written in the first computer language. The initial command is converted into a modified command processable by one or more applications written in a second computer language. The modified command is provided to a second microprocessor executing the one or more applications written in the second computer language.

One or more of the following features may be included. The one or more applications written in the first computer language may be chosen from the group consisting of an operating system, an executive loop and a software application. The one or more applications written in the second computer language may be chosen from the group consisting of an operating system, an executive loop and a software application.

The first microprocessor may be a primary microprocessor. The one or more applications written in the first computer language may be one or more primary applications. The second microprocessor may be a safety microprocessor. The one or more applications written in the second computer language may be one or more safety applications.

The first computer language may be chosen from the group consisting of Ada, Basic, Cobol, C, C++, C#, Fortran, Visual Assembler, Visual Basic, Visual J++, Java, and Java Script. The second computer language may be chosen from the group consisting of Ada, Basic, Cobol, C, C++, C#, Fortran, Visual Assembler, Visual Basic, Visual J++, Java, and Java Script.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
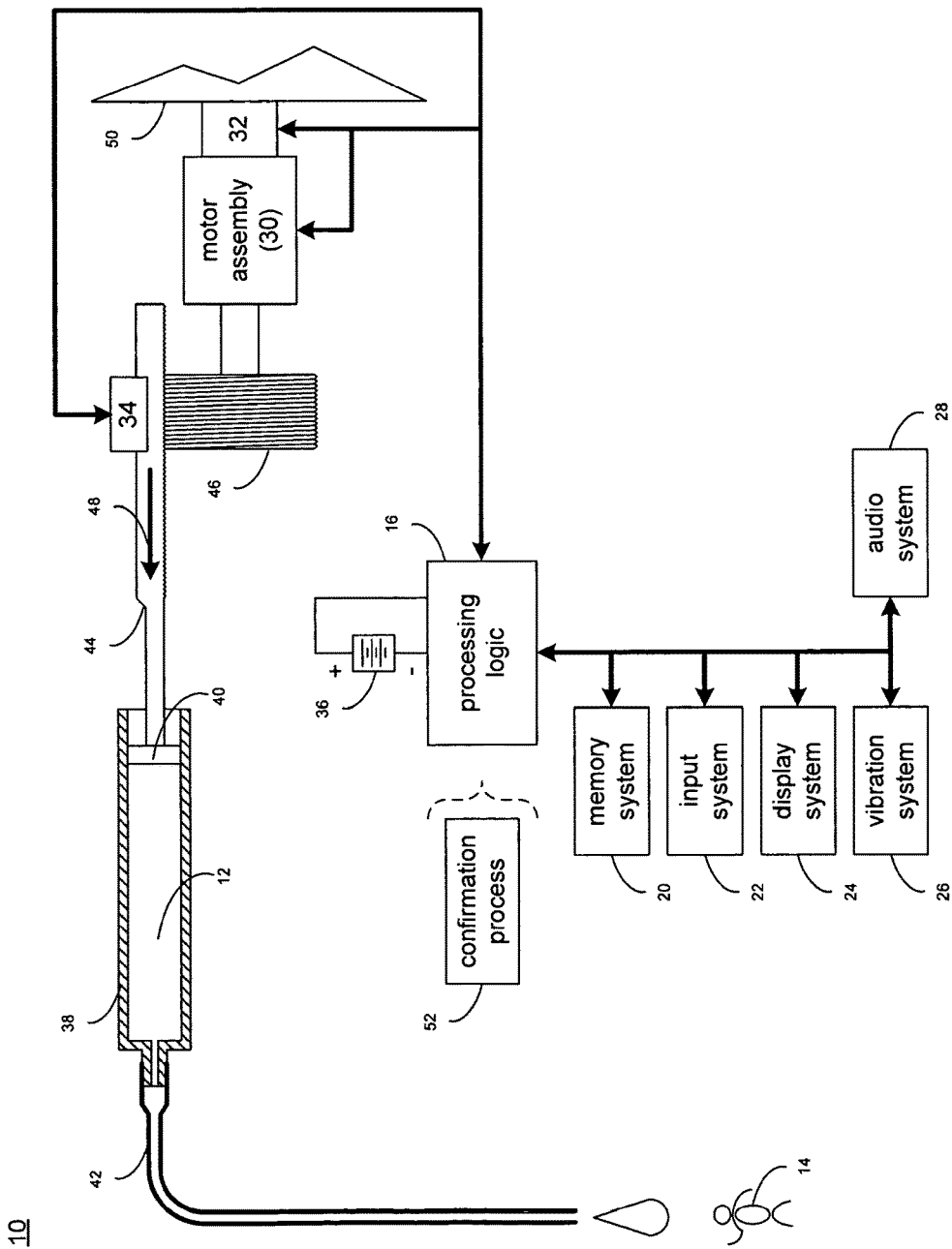
FIG. 1 is a diagrammatic view of an infusion pump assembly including processing logic that executes a confirmation process.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs.

Infusion pump assembly 10 may include processing logic 16 that executes one or more processes that may be required for infusion pump assembly 10 to operate properly. Processing logic 16 may include one or more microprocessors (to be discussed below in greater detail), one or more input/output controllers (not shown), and cache memory devices (not shown). One or more data buses and/or memory buses may be used to interconnect processing logic 16 with one or more subsystems.

Examples of such subsystems may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a first battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, the reservoir assembly 38 may be a reservoir assembly similar to that described in U.S. Patent Application Publication No. US-2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may forma pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the power to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to- digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 46, thus increasing the torque and resolution of motor assembly 30 by a factor of three-thousand.

Figure 2:
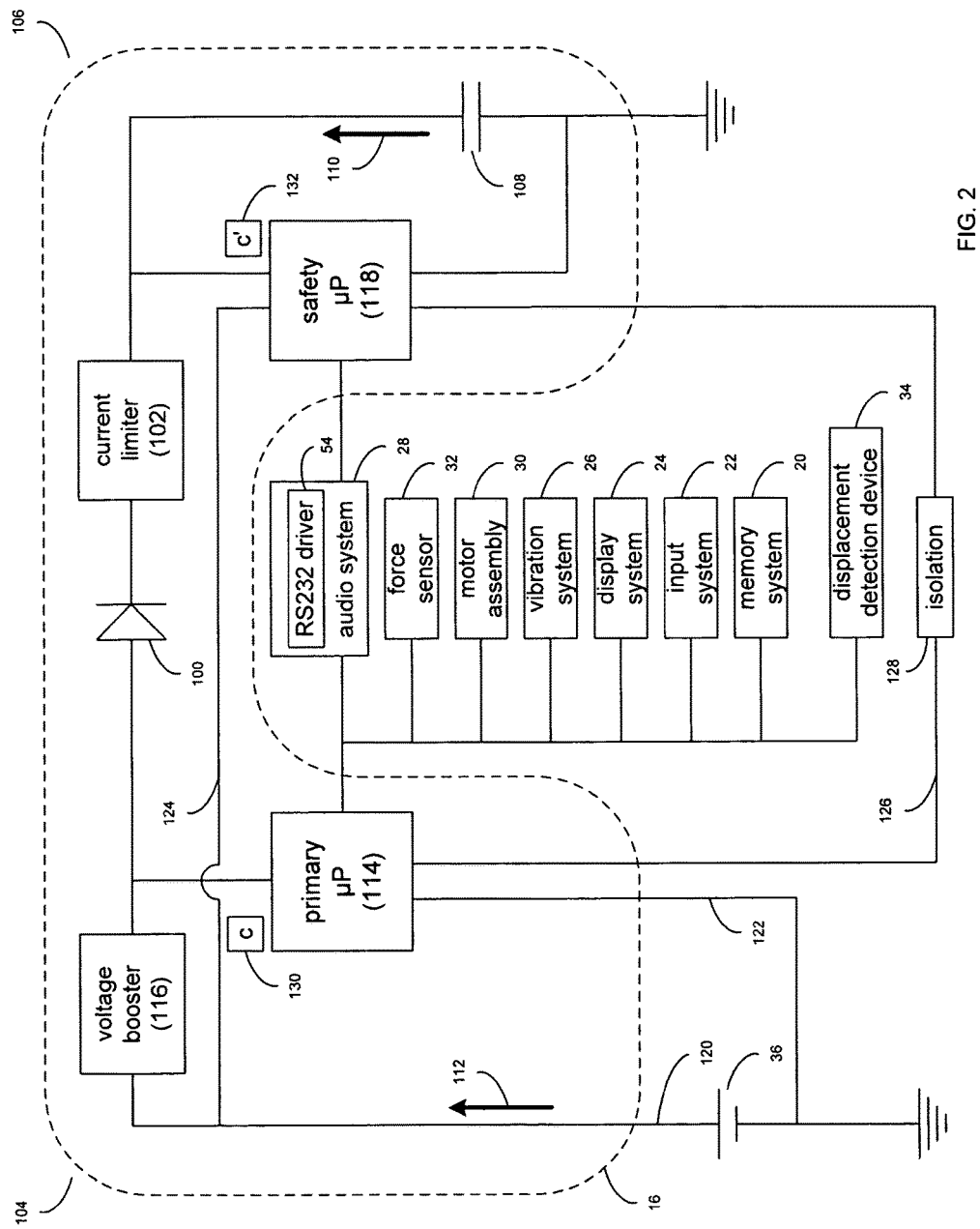
FIG. 2 is a more-detailed diagrammatic view of the processing logic of FIG. 1.

Referring also to FIG. 2, there is shown a more-detailed diagrammatic view of processing logic 16. Processing logic 16 may include one or more circuit partitioning components 100, 102 configured to divide processing logic 16 into primary processing logic 104 and backup processing logic 106. Examples of one or more circuit partitioning components 100, 102 may include but are not limited to diode assembly 100 and current limiting assembly 102.

Diode assembly 100 may be configured to allow primary power supply 36 to charge backup power supply 108 included within backup processing logic 106, while prohibiting backup power supply 108 from providing backup electrical energy 110 to primary processing logic 104 in the event that some form of failure prevents primary electrical energy 112 from providing primary processing logic 104. An example of backup power supply 108 may include but is not limited to a super capacitor assembly. An example of such a super capacitor assembly may include but is not limited to an electric double-layer capacitor manufactured by Elna Co. Ltd. of Yokohama, Japan.

Current limiting assembly 102 may be configured to limit the amount of primary electrical energy 112 available to charge backup power supply 108. Specifically, as primary power supply 36 may be configured to charge backup power supply 108, the amount of current available from primary power supply 36 may be limited to e.g., avoid depriving primary processing logic 104 of a requisite portion of primary electrical energy 112.

Primary processing logic 104 may include primary microprocessor 114 and voltage booster circuit 116. An example of primary microprocessor 114 may include but is not limited to a H8S/2000 manufactured by Renesas Technology America Inc. of San Jose, Calif. Voltage booster circuit 116 may be configured to increase the voltage potential of primary electrical energy 112 provided by primary power supply 36 to a level sufficient to power primary microprocessor 114. An example of voltage booster circuit 116 may include but is not limited to a LTC3421 manufactured by Linear Technology of Milpitas, Calif.

Current limiting assembly 102 may be configured to limit the amount of current available to charge backup power supply 108 during the power-up of primary microprocessor 114. Specifically and for illustrative purposes, current limiter assembly 102 may be controlled by primary microprocessor 114 and current limiting assembly 102 may be disabled (i.e., provide no charging current to backup power supply 108) until after primary microprocessor 114 is fully powered up. Upon primary microprocessor 114 being fully powered up, primary microprocessor 114 may now enable current limiting assembly 102, thus providing charging current to backup power supply 108. Alternatively and upon being initially energized, current limiting assembly 102 may be configured to prohibit the flow of charging current to backup power supply 108 for a time sufficient to allow for the powering up of primary microprocessor 114.

Backup processing logic 106 may include backup power supply 108 and safety microprocessor 118. An example of safety microprocessor 118 may include but is not limited to a MSP430 manufactured by Texas Instruments of Dallas, Tex.

Primary power supply 36 may be configured to provide primary electrical energy 112 to at least a portion of processing logic 16. Specifically and during normal operation of infusion pump assembly 10, primary power supply 36 may be configured to provide primary electrical energy 112 to all of processing logic 16 (including the various components of primary processing logic 104 and backup processing logic 106), as well as various subsystems included within infusion pump assembly 10.

Examples of such subsystems may include but are not limited to memory system 20, input system 22, display system 24, vibration system 26, audio system 28, motor assembly 30, force sensor 32, and displacement detection device 34.

Backup power supply 108 may be configured to provide backup electrical energy 110 to the at least a portion of processing logic 16 in the event that primary power supply 36 fails to provide primary electrical energy 112 to at least a portion of processing logic 16. Specifically, in the event that primary power supply 36 fails and, therefore, can no longer provide primary electrical energy 112 to processing logic 16, backup power supply 108 may be configured to provide backup electrical energy 110 to backup processing logic 106.

For illustrative purposes only, assume that infusion pump assembly is operating normally and primary power supply 36 is providing primary electrical energy 112 to processing logic 16. As discussed above, voltage booster circuit 116 may increase the voltage potential of primary electrical energy 112 to a level sufficient to power primary microprocessor 114, wherein voltage booster circuit 116 and primary microprocessor 114 are both included within primary processing logic 104.

Further, diode assembly 100 may allow a portion of primary electrical energy 112 to enter backup processing logic 106, thus enabling the operation of safety microprocessor 118 and the charging of backup power supply 108. As discussed above an example of backup power supply 108 may include but is not limited to a super capacitor. As discussed above, current limiter assembly 102 may limit the quantity of current provided by primary power supply 36 to backup processing logic 106, thus preventing the diversion of too large a portion of primary electrical energy 112 from primary processing logic 104 to backup processing logic 106.

Accordingly, in addition to powering safety microprocessor 118, primary power supply 36 may charge backup power supply 108. In a preferred embodiment, backup power supply 108 is a 0.33 farad super capacitor.

Safety microprocessor 118 may monitor the status of primary power supply 36 by monitoring the voltage potential present at the input of voltage booster circuit 116. Alternatively, safety microprocessor 118 may monitor the status of primary power supply 36 by e.g. monitoring (via conductor 124) the voltage potential present at the output of voltage booster circuit 116. Alternatively, safety microprocessor 118 may monitor the status of primary power supply 36 by monitoring the voltage potential present at the input of voltage booster circuit 116. Further still, safety microprocessor 118 and primary microprocessor 114 may be electrically-coupled via e.g. conductor 126 and primary microprocessor 114 may be configured to continuously provide a "beacon" signal to safety microprocessor 118. Conductor 126 may include isolation circuit 128 (e.g., one or more diodes assemblies) to electrically isolate safety microprocessor 118 and primary microprocessor 114. Accordingly, provided safety microprocessor 118 continues to receive the "beacon" signal from primary microprocessor 114, primary microprocessor 114 is functioning and, therefore, being properly powered by primary power supply 36. In the event that safety microprocessor 118 fails to receive the "beacon" signal from primary microprocessor 114, an alarm sequence may be initiated.

Further still, safety microprocessor 118 may be configured to continuously provide a "beacon" signal to primary microprocessor 114. Accordingly, provided primary microprocessor 114 continues to receive the "beacon" signal from safety microprocessor 118, safety microprocessor 118 is functioning and, therefore, being properly powered by backup power supply 108. In the event that primary microprocessor 114 fails to receive the "beacon" signal from safety microprocessor 118, an alarm sequence may be initiated.

As used in this disclosure, a "beacon" signal may be considered an event that is performed by primary microprocessor 114 (and/or safety microprocessor 118) solely for the purpose of making the presence of primary microprocessor 114 (and/or safety microprocessor 118) known. Additionally/alternatively, the "beacon" signal may be considered an event that is performed by primary microprocessor 114 (and/or safety microprocessor 118) for the purpose of performing a task, wherein the execution of this event is monitored by safety microprocessor 118 (and/or primary microprocessor 114) to confirm the presence of primary microprocessor 114 (and/or safety microprocessor 118).

Assume for illustrative purposes that primary power supply 36 fails. For example, assume that primary power supply 36 physically fails (as opposed to simply becoming discharged). Examples of such a failure may include but are not limited to the failing of a cell (not shown) within primary power supply 36 and the failing of a conductor (e.g., one or more of conductors 120, 122) that electrically-couples primary power supply 36 to processing logic 16. Accordingly, in the event of such a failure, primary power supply 36 may no longer provide primary electrical energy 112 to processing logic 16.

However, when such a failure of primary power supply 36 occurs, the voltage potential present at the output of voltage booster circuit 116 and the voltage potential present at the input of voltage booster circuit 116 may be reduced to zero. Since safety microprocessor 118 may monitor (as discussed above) one or more of these voltage potentials, safety microprocessor 118 may be knowledgeable that primary power supply 36 has failed.

Further, when such a failure of primary power supply 36 occurs, primary microprocessor 114 will no longer be powered and, therefore, primary microprocessor 141 will no longer produce the above-described "beacon" signals. Since safety microprocessor 118 monitors the above-described "beacon" signals, safety microprocessor 118 may be knowledgeable that primary power supply 36 has failed.

As discussed above, in the event of such a failure of primary power supply 36, as diode assembly 100 is reversed-biased, backup power supply 108 may not provide backup electrical energy 110 to primary processing logic 104. Accordingly, primary processing logic 104 will know longer function.

Upon sensing the failure of primary power supply 36, safety microprocessor 118 may initiate an alarm sequence that may result in audio system 28 being energized. Audio system 28 may be controllable by both safety microprocessor 118 and primary microprocessor 114. Alternatively, a separate audio system may be used for each of safety microprocessor 118 and primary microprocessor 114. An example of audio system 118 may include but is not limited to a Piezo electric diaphragm, an example of which may include but is not limited to a 7BB-15-6 manufactured by Murata of Kyoto, Japan.

Audio system 28 may further include an RS232 line driver circuit 54, such as a MAX3319/MAX3221 manufactured by Maxim Integrated Products of Sunnyvale, CA. One or more of primary microprocessor 114 and safety microprocessor 118 may be configured to provide an alarm control signal (e.g., a square wave; not shown) to RS232 line driver circuit 52 to generate an alarm output signal (not shown) that may be provided to and may drive the above-described Piezo electric diaphragm.

The alarm sequence initiated by safety microprocessor 118 is intended to inform user 14 of the failure of primary power supply 36 so that user 14 may take the appropriate action (e.g. seeking an alterative means to have their therapy performed and/or having infusion pump assembly 10 repaired/replaced). Backup power supply 108 may be sized so that safety microprocessor 118 and audio system 28 may continue to function for up to fifteen minutes or more after the failure of primary power supply 36 (i.e., depending on design specifications).

The alarm sequence initiated by safety microprocessor 118 and/or primary microprocessor 114 may be an "escalating" alarm sequence in some embodiments. For example, at first a discrete "vibrating" alarm may be initiated (via vibration system 26). In the event that this "vibrating" alarm is not acknowledged within a defined period of time (e.g., one minute), a low volume audible alarm may be initiated. In the event that this low volume alarm is not acknowledged within a defined period of time (e.g., one minute), a medium volume audible alarm may be initiated. In the event that this medium volume alarm is not acknowledged within a defined period of time (e.g., one minute), a high volume audible alarm may be initiated. The escalating alarm sequence may provide a notification to user 14, in which the notification may be discrete or less disruptive at the onset. The initially discrete or less disruptive notification may be advantageous as user 14 may experience minimal disruption. However, in the event that user 14 does not acknowledge the alarm, the escalating nature of the alarm may provide for additional layers of safety to user 14. Additionally, in a case of audio system 28 error, or vibration system 26 error, the escalating alarm sequence, which may include both vibration and audio alarms, may insure that user 14 may be notified regardless of whether both systems 26, 28 are functioning.

Audio system 28, in some embodiments, may be configured to perform a self test upon power up. For example, upon infusion pump assembly 10 being initially powered up, audio system 28 may provide a "beep-type" signal to each sound generating device included within audio system 28. In the event that user 14 does not hear these "beep-type" signal(s), user 14 may take the appropriate action (e.g. seeking an alterative means to have their therapy performed and/or having infusion pump assembly 10 repaired/replaced). As discussed above, audio system 28 may be controllable by safety microprocessor 118 and/or primary micro-processor 114. Accordingly, when performing the above-described self test upon power up, safety microprocessor 118 and/or primary microprocessor 114 may control the above-described self test. This feature may provide for additional safety to user 14, as user 14 may be alerted to a system error earlier than may otherwise be the case. Thus, a method may be provided to notify the user early of system errors. Also, the system may otherwise not be aware of an error in audio system 28, thus, this feature provides for identification of a failure by user 14 that may otherwise go undetected.

During the failure of primary power supply 36, safety microprocessor 118 may continue to monitor the voltage potential present at the output of voltage booster circuit 116 and/or the voltage potential present at the input of voltage booster circuit 116. Additionally, safety microprocessor 118 may continue to monitor for the presence of the above-described "beacon" signals. Accordingly, in the event that the failure of primary power supply 36 was a temporary event (e.g. primary power supply 36 is an out-of-date battery and is being replaced with a new battery), safety microprocessor 118 may be knowledgeable when primary power supply 36 is once again functioning properly.

Upon primary power supply 36 once again functioning properly, diode assembly 100 and current limiting assembly 102 may allow a portion of primary electrical energy 112 produced by primary power supply 36 to recharge backup power supply 108.

Additionally, safety microprocessor 118 and primary microprocessor 114 may each maintain a real-time clock, so that the various doses of infusible fluid may be dispensed at the appropriate time of day. As primary microprocessor 114 was not functioning during the failure of primary power supply 36, the real-time clock maintained within primary microprocessor 114 may no longer be accurate. Accordingly, the real-time clock maintained within safety microprocessor 118 may be used to reset the real-time clock maintained within primary microprocessor 114.

In order to further enhance the reliability and safety of infusion pump assembly 10, primary microprocessor 114 and safety microprocessor 118 may each execute applications written in different programming languages. For example, primary microprocessor 114 may be configured to execute one or more primary applications written in a first computer language, while safety microprocessor 118 may be configured to execute one or more safety applications written in a second computer language.

Examples of the first computer language in which the primary applications are written may include but are not limited to Ada, Basic, Cobol, C, C++, C#, Fortran, Visual Assembler, Visual Basic, Visual J++, Java, and Java Script languages. In a preferred embodiment, the first computer language in which the primary applications (executed on primary microprocessor 114) are written is the C++ computer language.

Examples of the second computer language in which the safety applications are written may include but are not limited to Ada, Basic, Cobol, C, C++, C#, Fortran, Visual Assembler, Visual Basic, Visual J++, Java, and Java Script languages. In a preferred embodiment, the second computer language in which the safety applications (executed on safety microprocessor 118) are written is the C computer language.

Further, assuming that primary microprocessor 114 and safety microprocessor 118 are different types of microprocessors and, therefore, use different compilers; the compiled code associated with the primary applications executed by primary microprocessor 114 and the safety applications executed on safety microprocessor 118 may be different (regardless of the whether the primary applications and the safety applications were written in the same computer language.

Examples of the one or more primary applications written in the first computer language and executable on primary microprocessor 114 may include but are not limited to an operating system (e.g., Linux™, Unix™, Windows CE™), an executive loop and various software applications. Further, examples of the one or more safety applications written in the second computer language and executable on safety microprocessor 118 may include but are not limited to an operating system (e.g., Linux™, Unix™, Windows CE™), an executive loop and various software applications.

Accordingly, primary processing logic 104 and backup processing logic 106 may each be configured as a separate stand-alone autonomous computing device. Therefore, primary microprocessor 114 included within primary processing logic 104 may execute a first operating system (e.g. Linux™) and safety microprocessor 118 included within backup processing logic 106 may execute an executive loop.

Additionally, primary microprocessor 114 included within primary processing logic 104 may execute one or more software applications (e.g. graphical user interface applications, scheduling applications, control applications, telemetry applications) executable within (in this example) a Linux™ operating system. Further, safety microprocessor 118 included within backup processing logic 106 may execute one or more software applications (e.g. graphical user interface applications, scheduling applications, control applications, telemetry applications) executable within (in this example) the executive loop.

By utilizing diverse computer languages and/or diverse operating systems, infusion pump assembly may be less susceptible to e.g. computer-language bugs, operating-system bugs, and/or computer viruses.

One or more of primary microprocessor 114 (included within primary processing logic 104 of processing logic 16) and safety microprocessor 118 (included within backup processing logic 106 of processing logic 16) may execute confirmation process 52 (FIG. 1). As will be discussed below in greater detail, confirmation process 52 may be configured to process a command received on a first microprocessor (e.g., primary microprocessor 114) so that the command may be confirmed by a second microprocessor (e.g., safety microprocessor 118).

The instruction sets and subroutines of confirmation process 52, which may be stored on a storage device (e.g., memory system 20) accessible by processing logic 16, may be executed by one or more processors (e.g., primary microprocessor 114 and/or safety microprocessor 118) and one or more memory architectures (e.g., memory system 20) included within infusion pump assembly 10. Examples of memory system 20 may include but are not limited to: a random access memory; a read-only memory; and a flash memory.

Figure 3:
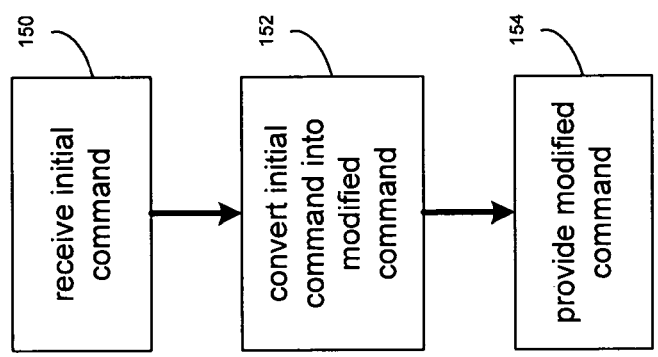
FIG. 3 is a flowchart of the confirmation process of FIG. 1.

Referring also to FIG. 3, confirmation process 52 may receive 150, on a first microprocessor executing one or more applications written in a first computer language, an initial command processable by the one or more applications written in the first computer language. For example and as discussed above, primary microprocessor 114 (included within primary processing logic 104) may be executing the Linux™ operating system. Assuming that user 14 wishes to have a 0.50 mL dose of infusible fluid 12 dispensed by infusion pump assembly 12, user 14 may select (via input system 22 and display system 24) the appropriate commands to have the 0.50 mL dose dispensed. Accordingly, primary microprocessor 114 may receive 150 a corresponding command (e.g., command 130) to dispense 0.50 mL of infusible fluid 12.

As discussed above, safety microprocessor 118 (included within backup processing logic 106) may be executing the executive loop. Accordingly, command 130 may not be provided to safety microprocessor 118 in its native form, as safety microprocessor 118 may not be capable of processing command 130, due to safety microprocessor 118 executing the executive loop and primary microprocessor 114 executing the Linux™ operating system.

Accordingly, confirmation process 52 may convert 152 initial command 130 into a modified command (e.g., command 132) that may be processable by e.g., safety microprocessor 118 (included within backup processing logic 106) that may be executing protocol (not shown) that effectuates the communication of primary microprocessor 114 and safety microprocessor 118. Once command 130 is converted 152 into modified command 132, modified command 132 may be provided 154 to e.g., safety microprocessor 118 (included within backup processing logic 106) that may be executing e.g., the executive loop.

Once received by e.g., safety microprocessor 118 (included within backup processing logic 106), safety microprocessor 118 may process modified command 132 and provide (via e.g., display system 24) a visual confirmation to user 14. Prior to processing modified command 132, confirmation process 52 may convert modified command 132 into a native command (not shown) processable by safety microprocessor 118. For example, upon receiving modified command 132, safety microprocessor 118 may process received modified command 132 to render (on display system 24) a visual confirmation.

Upon processing modified command 132, confirmation process 52 may render on display system 24 a message that states "Dispense 0.50 U Dose?". Upon reading this message, user 14 may either authorize the dispensing of the 0.50 mL dose or cancel the dispensing of the 0.50 mL dose. Accordingly, if user 14 authorizes the dispensing of the 0.50 mL dose of infusible fluid 12, the accuracy of command 130 and command 132 are both confirmed. However, in the event that e.g., the message rendered by confirmation process 52 is incorrect (e.g., "Dispense 1.50 U Dose?"), the conversion 152 of command 130 to command 132 has failed. Accordingly, primary microprocessor 114 (and/or the applications being executed on primary microprocessor 114) and/or safety microprocessor 118 (and/or the applications being executed on safety microprocessor 118) may be malfunctioning. Accordingly, user 14 may need to seek an alternative means to having their therapy performed and/or have infusion pump assembly 10 serviced. Accordingly, the operational safety and reliability of infusion pump assembly 10 may be enhanced as any command received is confirmed as being correct by both primary microprocessor 114, safety microprocessor 118, and user 14.

A number of implementations have been described. Nevertheless, it will be understood that various modifications may be made. Accordingly, other implementations are within the scope of the following claims.

What is claimed is:

1. An infusion pump assembly comprising:
   a reservoir assembly configured to contain an infusible fluid;
   a motor assembly configured to act upon the reservoir assembly and dispense at least a portion of the infusible fluid contained within the reservoir assembly;
   processing logic configured to control the motor assembly;
   wherein the processing logic includes:
      a primary microprocessor configured to execute one or more primary applications written in a first computer language; and
      a safety microprocessor configured to execute one or more safety applications written in a second computer language that is different than the first computer language; and
   a computer program product residing on a computer readable medium having a plurality of instructions stored thereon which, when executed by a processor, cause the processor to perform operations comprising:
      receiving, on the primary microprocessor executing the one or more primary applications written in the first computer language, an initial command processable by the one or more primary applications written in the first computer language;
      converting the initial command into a modified command processable by the one or more safety applications written in the second computer language; and
      providing the modified command to the safety microprocessor executing the one or more safety applications written in the second computer language.

2. The infusion pump assembly of claim 1 further comprising:
   a primary power supply configured to provide primary electrical energy to at least a portion of the processing logic; and a backup power supply configured to provide backup electrical energy to the at least the portion of the processing logic in an event that the primary power supply fails to provide the primary electrical energy to the at least the portion of the processing logic.

3. The infusion pump assembly of claim 2 wherein:
the primary power supply is a first battery; and
the backup power supply is a super capacitor assembly.

4. The infusion pump assembly of claim 1 wherein the processing logic includes one or more circuit partitioning components configured to divide the processing logic into primary processing logic and backup processing logic.

5. The infusion pump assembly of claim 4 wherein the primary processing logic includes the primary microprocessor.

6. The infusion pump assembly of claim 4 wherein the backup processing logic includes the safety microprocessor.

7. The infusion pump assembly of claim 4 wherein the one or more circuit partitioning components includes one or more of a diode assembly and a current limiting assembly.

8. The infusion pump assembly of claim 7 wherein the diode assembly is configured to allow a primary power supply to charge a backup power supply while prohibiting the backup power supply from providing backup electrical energy to the primary processing logic in an event that the primary power supply fails to provide a primary electrical energy to the primary processing logic.

9. The infusion pump assembly of claim 1 wherein the one or more primary applications written in the first computer language are chosen from a group consisting of an operating system, an executive loop and a software application.

10. The infusion pump assembly of claim 1 wherein the one or more safety applications written in the second computer language are chosen from a group consisting of an operating system, an executive loop and a software application.

11. The infusion pump assembly of claim 1 wherein a primary power supply is configured to provide electrical energy to one or more subsystems included within the infusion pump assembly.

12. The infusion pump assembly of claim 1 wherein a primary power supply and a backup power supply are configured to provide electrical energy to an audio system included within the infusion pump assembly.

13. The infusion pump assembly of claim 12 wherein the audio system is configured to provide an escalating alarm sequence in the event of a loss of a beacon signal, wherein the escalating alarm sequence includes at least a low-intensity alarm and a high-intensity alarm.

14. The infusion pump assembly of claim 1 wherein the first computer language is chosen from a group consisting of Ada, Basic, Cobol, C, C++, C#, Fortran, Visual Assembler, Visual Basic, Visual J++, Java, and Java Script.

15. The infusion pump assembly of claim 1 wherein the second computer language is chosen from a group consisting of Ada, Basic, Cobol, C, C++, C#, Fortran, Visual Assembler, Visual Basic, Visual J++, Java, and Java Script.

16. An infusion pump assembly comprising:
a reservoir assembly configured to contain an infusible fluid;
a motor assembly configured to act upon the reservoir assembly and dispense at least a portion of the infusible fluid contained within the reservoir assembly;
processing logic configured to control the motor assembly;
wherein the processing logic includes:
one or more circuit partitioning components configured to divide the processing logic into primary processing logic and backup processing logic;
a primary microprocessor included within the primary processing logic and configured to execute one or more primary applications written in a first computer language;
a safety microprocessor included within the backup processing logic and configured to execute one or more safety applications written in a second computer language that is different than the first computer language; and
a computer program product residing on a computer readable medium having a plurality of instructions stored thereon which, when executed by a processor, cause the processor to perform operations comprising:
receiving, on the primary microprocessor executing the one or more primary applications written in the first computer language, an initial command processable by the one or more primary applications written in the first computer language;
converting the initial command into a modified command processable by the one or more safety applications written in the second computer language; and
providing the modified command to the safety microprocessor executing the one or more safety applications written in the second computer language.

17. The infusion pump assembly of claim 16 wherein the one or more primary applications written in the first computer language are chosen from a group consisting of an operating system, an executive loop and a software application.

18. The infusion pump assembly of claim 16 wherein the one or more safety applications written in the second computer language are chosen from a group consisting of an operating system, an executive loop and a software application.

19. The infusion pump assembly of claim 16 further comprising:
a primary power supply configured to provide primary electrical energy to at least a portion of the processing logic; and
a backup power supply configured to provide backup electrical energy to the at least the portion of the processing logic in an event that the primary power supply fails to provide the primary electrical energy to the at least the portion of the processing logic.

20. The infusion pump assembly of claim 16 wherein the first computer language is chosen from a group consisting of Ada, Basic, Cobol, C, C++, C#, Fortran, Visual Assembler, Visual Basic, Visual J++, Java, and Java Script.

21. The infusion pump assembly of claim 16 wherein the second computer language is chosen from a group consisting of Ada, Basic, Cobol, C, C++, C#, Fortran, Visual Assembler, Visual Basic, Visual J++, Java, and Java Script.

* * * * *